(12) United States Patent
Eriksson et al.

(10) Patent No.: US 8,752,502 B2
(45) Date of Patent: Jun. 17, 2014

(54) DEVICE FOR STABILIZATION AND VISUAL MONITORING OF AN ELONGATED METALLIC STRIP IN A TRANSPORT DIRECTION ALONG A PREDETERMINED TRANSPORT PATH

(75) Inventors: Boo Eriksson, Vasteras (SE); Mats Molander, Vasteras (SE); Peter Lofgren, Vasteras (SE)

(73) Assignee: ABB Research Ltd. (CH)

( * ) Notice: Subject to any disclaimer, the term of this patent is extended or adjusted under 35 U.S.C. 154(b) by 453 days.

(21) Appl. No.: 12/731,507

(22) Filed: Mar. 25, 2010

(65) Prior Publication Data

US 2010/0209591 A1  Aug. 19, 2010

Related U.S. Application Data

(63) Continuation of application No. PCT/EP2008/061840, filed on Sep. 8, 2008.

(30) Foreign Application Priority Data

Sep. 25, 2007  (SE) ..................................... 0702163

(51) Int. Cl.
| | | |
|---|---|---|
| B05C 11/00 | (2006.01) | |
| B05C 3/12 | (2006.01) | |
| G06K 9/00 | (2006.01) | |
| B05C 11/06 | (2006.01) | |
| C23C 16/52 | (2006.01) | |
| B05D 3/04 | (2006.01) | |
| B05D 1/18 | (2006.01) | |

(52) U.S. Cl.
CPC ..................................... *B05C 11/06* (2013.01)
USPC ............. 118/672; 118/62; 118/419; 118/668; 118/670; 118/713; 427/8; 427/348; 427/431; 382/141

(58) Field of Classification Search
CPC ........ B05C 3/125; B05C 3/0406; C23C 2/40; C23C 2/16
USPC .............. 427/8, 9; 118/663, 62, 63, 419, 420, 118/429, 668, 670–672, 712, 713; 72/37; 358/106; 382/141, 145, 151, 152, 382; 348/125; 356/237.1, 429; 425/113
See application file for complete search history.

(56) References Cited

U.S. PATENT DOCUMENTS

| | | | | | |
|---|---|---|---|---|---|
| 3,998,181 | A | * | 12/1976 | Bellen et al. .................. | 118/665 |
| 4,135,006 | A | * | 1/1979 | Readal et al. .................. | 427/10 |
| 4,539,561 | A | * | 9/1985 | Wulff ............................ | 340/675 |
| 4,675,730 | A | * | 6/1987 | Adomaitis et al. ............. | 348/131 |
| 4,865,872 | A | * | 9/1989 | Pellatiro ......................... | 427/9 |
| 5,074,242 | A | * | 12/1991 | Bricmont ....................... | 118/665 |
| 5,087,822 | A | | 2/1992 | Fairlie et al. | |
| 5,239,376 | A | * | 8/1993 | Dittmann et al. .............. | 348/88 |
| 5,263,094 | A | * | 11/1993 | Laitinen et al. ............... | 382/152 |
| 5,305,099 | A | * | 4/1994 | Morcos ......................... | 348/88 |
| 5,307,152 | A | * | 4/1994 | Boehnlein et al. ............ | 356/605 |
| 5,313,069 | A | * | 5/1994 | Tham ....................... | 250/559.26 |
| 5,427,161 | A | * | 6/1995 | Luhmann et al. ............. | 141/144 |
| 5,679,161 | A | * | 10/1997 | Wysokowski et al. ........ | 118/669 |
| 5,786,036 | A | * | 7/1998 | Pannenbecker et al. ...... | 427/444 |
| 5,996,384 | A | * | 12/1999 | Steeper et al. .................... | 72/37 |
| 6,266,436 | B1 | * | 7/2001 | Bett et al. ...................... | 382/141 |
| 6,290,776 | B1 | * | 9/2001 | Tada et al. ..................... | 118/405 |
| 6,378,572 | B1 | * | 4/2002 | Neubauer et al. .............. | 141/94 |
| 6,464,788 | B2 | * | 10/2002 | Falck et al. .................... | 118/602 |
| 6,471,153 | B1 | | 10/2002 | Kimura et al. | |
| 6,725,123 | B1 | * | 4/2004 | Denuell ........................ | 700/122 |
| 7,425,982 | B2 | * | 9/2008 | Joskin et al. .................. | 348/142 |
| 7,445,209 | B2 | * | 11/2008 | Sano et al. .................... | 271/263 |
| 7,553,375 | B2 | * | 6/2009 | Sekiya ............................. | 118/62 |
| 7,669,638 | B2 | * | 3/2010 | Kollberg et al. ........... | 164/154.5 |
| 7,712,502 | B2 | * | 5/2010 | Engelbart et al. ............. | 156/351 |
| 8,000,501 | B2 | * | 8/2011 | Huotilainen .................. | 382/108 |
| 8,429,834 | B2 | * | 4/2013 | Fujioka et al. .................. | 34/623 |
| 8,483,474 | B2 | * | 7/2013 | Monfort ........................ | 382/141 |
| 2003/0066400 | A1 | * | 4/2003 | Noe et al. .......................... | 83/34 |
| 2003/0077397 | A1 | * | 4/2003 | Kabeya et al. ................ | 427/431 |
| 2004/0050323 | A1 | * | 3/2004 | Chae ............................. | 118/400 |
| 2004/0095571 | A1 | * | 5/2004 | Bourely et al. ............ | 356/237.1 |
| 2004/0157175 | A1 | * | 8/2004 | Matsumoto et al. .......... | 430/605 |
| 2004/0168556 | A1 | * | 9/2004 | Noe et al. .......................... | 83/35 |
| 2008/0044584 | A1 | * | 2/2008 | Eriksson et al. ............ | 427/430.1 |
| 2009/0175708 | A1 | * | 7/2009 | Lofgren et al. .......... | 414/222.02 |

| | | | | |
|---|---|---|---|---|
| 2009/0208665 A1* | 8/2009 | Eriksson et al. | | 427/547 |
| 2011/0086457 A1* | 4/2011 | Yokoyama | | 438/57 |
| 2011/0217481 A1* | 9/2011 | Ohara et al. | | 427/547 |
| 2012/0308244 A1* | 12/2012 | Watanabe et al. | | 399/16 |

FOREIGN PATENT DOCUMENTS

| | | | | |
|---|---|---|---|---|
| EP | 0813703 B1 | 12/1997 | | |
| JP | 9113465 A | 5/1997 | | |
| JP | 9184055 A | 7/1997 | | |
| WO | 02101366 A1 | 12/2002 | | |
| WO | WO 2004050277 | * | 6/2004 | B22D 11/16 |
| WO | 2006006911 A1 | 1/2006 | | |
| WO | WO 2006021437 | * | 4/2006 | C23C 2/14 |
| WO | 2006101446 A1 | 9/2006 | | |
| WO | WO 2007003685 | * | 1/2007 | G06K 9/00 |
| WO | WO 2007004945 | * | 1/2007 | C23C 2/14 |

OTHER PUBLICATIONS

International Search Report and Written Opinion of the International Searching Authority; PCT/EP2008/061840; Jan. 20, 2010; 11 pages.

\* cited by examiner

*Primary Examiner* — Yewebdar Tadesse
*Assistant Examiner* — Karl Kurple

(74) *Attorney, Agent, or Firm* — St. Onge Steward Johnston & Reens LLC

(57) ABSTRACT

A device and a method for visual monitoring and stabilization of an elongated metallic strip during continuous transport of the strip in a transport direction along a predetermined transport path, wherein the strip has been coated with a metallic layer by the strip having continuously passed through a bath of molten metal. The device includes an electromagnetic stabilizing device with at least one first pair of electromagnetic stabilizing means arranged on each side of the predetermined transport path, and a wiping device for wiping off superfluous molten metal from the strip by applying an air current in a line transversely of the transport direction of the strip and across essentially the whole width of the strip. A first image-reading apparatus takes images of the actual position of the strip in relation to the predetermined transport path. A second and third image-reading apparatus take images of the surface of the strip.

8 Claims, 2 Drawing Sheets

DEVICE FOR STABILIZATION AND VISUAL MONITORING OF AN ELONGATED METALLIC STRIP IN A TRANSPORT DIRECTION ALONG A PREDETERMINED TRANSPORT PATH

CROSS-REFERENCE TO RELATED APPLICATIONS

The present application is a continuation of pending International patent application PCT/EP2008/061840 filed on Sep. 8, 2008 which designates the United States and claims priority from Swedish patent application 0702163-7 filed on Sep. 25, 2007, the content of which is incorporated herein by reference.

FIELD OF THE INVENTION

This present invention relates to a device for improving the surface quality and effectively stabilizing an elongated metallic strip, and to a method for improving the surface quality and effectively stabilizing said strip.

BACKGROUND OF THE INVENTION

When continuously coating, for example with a layer of metal, elongated metallic strips, for example steel sheet, the strip continuously passes through a bath containing molten metal, usually zinc or aluminium. In the bath, the strip usually passes below a roller immersed in the metal bath and thereafter moves upwards through stabilizing and correcting rollers. The strip emerges from the bath and is transported through a wiping device composed of a set of air-knives, intended to blow off superfluous molten metal from the strip and further back to the bath, to control the thickness of the coating. The gas that is blown out with the knives is usually air or nitrogen gas, but also steam or inert gas may be used. The strip is then transported without support until the coating has been cooled down and solidified. The coated strip is then led or directed via an upper roller for continued processing of the strip, such as, for example, cutting of the strip into separate sheet element or for winding the strip onto a roller. In the normal case, the strip moves in a vertical direction from the roller immersed into the bath through the correcting and stabilizing rollers and the air-knives to the upper roller.

To stabilize the strip, there is used an electromagnetic stabilizing device that is designed to stabilize the position of the strip with respect to a predetermined transport path. The stabilizing device comprises at least a first pair of electromagnetic stabilizing means placed on respective sides of the strip.

When elongated metallic strips, for example steel sheet, are continuously coated with a layer of metal, a uniform and thin coating thickness is aimed at. To achieve this, it is common practice to measure the mass of the coating after the strip has passed through the upper roller, and then to utilize this reading for controlling the air-knives, which are usually located suspended from a beam movably arranged in the vertical direction in a direction towards the strip and arranged so that they may also be angled such that the angle at which the gas hits the coating on the strip may be changed, thus controlling the thickness of the coating.

Due to the geometry of the strip, the distance that the strip must run without any support, its speed and the blowing effect of the air-knives, however, the strip will move or vibrate in a direction that is essentially perpendicular to its direction of transport. It has long been known to deal with this problem of transversal movements by using correcting and stabilizing rollers, a more precise control of the gas flow from the air-knives, and an adjustment of the speed of the strip and/or an adjustment of the distance over which the strip has to run without support. However, if these transversal movements are not reduced, these movements will considerably disturb the exact wiping of the air-knives, which subsequently results in an uneven thickness of the coating which may be visible to the naked eye. At present, it is difficult to establish by means of measurement equipment how uneven the coating thickness is after the strip has passed through the air-knives and the electromagnetic stabilizing device. The difficulty arises from the fact that the measurement occurs slowly, typically around 1-2 Hz, and only at one point of the strip at a time. If the strip then moves at a speed of, for example, 2 m/s, this means that it is not possible to automatically see local defects in the coating thickness or if there is an uneven coating thickness, which manifests itself in the form of stripes on the strip, without using manual/visual inspection of the strip. Horizontal stripes on the strip may have a repetition that corresponds to a frequency of 10 Hz or more, and if there are vertical stripes on the strip these are also very difficult to detect, even if an automatic thickness sensor that traverses is used.

Instead, the control of the coating thickness today occurs by an operator who manually, by visual inspection, controls the strip as the strip passed through the air-knives and the electromagnetic stabilizing equipment a long time ago, and then, if need arises, controls the air-knives and the electromagnets. Because of this late control, there is thus a risk that several meters of the strip are given an inferior surface quality, which means that a considerable amount of the quality of the strip will subsequently have to be downgraded and, in the worst case, be rejected.

Japanese patent specification with publication No. JP-09-202955 shows how the vibrations in a metallic strip may be reduced with the aid of rollers that stabilize and stretch the strip when it has passed the air-knives. The position of the strip in relation to its direction of transport in a plane is measured with a sensor, from where information is forwarded to a computer that carries out a vibration analysis based on the values obtained and together with information about the speed of the strip calculates the optimal tensioning of the strip in order to control the vibrations in the strip.

Japanese patent specification JP 3173755 describes a device for galvanizing a metallic strip, where stabilizing devices are arranged to reduce the vibrations of the strip. The stabilizing devices comprise guide devices arranged at and in contact with the corners of the respective edge of the strip to fix the edges in the desired position as well as an electromagnet arranged in a region opposite to the width of the strip, on opposite sides of the strip and between the respective guide device, to reduce the vibrations of the strip.

One problem with the above-mentioned devices is that they do not provide sufficient stabilization of the strip, and that the devices do not solve the problems of the surface quality of the strip.

In addition, it is known from, for example, U.S. Pat. No. 6,471,153 and WO 2006/101446, to use a plurality of electromagnets, arranged along the width of the strip, which generate magnetic forces acting perpendicular to the strip to damp transversal movements. Sensors are arranged to measure the distance between the strip and the electromagnets and a guide device guides the flow, based on the distance between the strip and the electromagnets that is measured by the sensors, of current through the electromagnets in order thus to damp the transversal movements to ensure that the position of the strip in relation to the predetermined transport path does not deviate too much.

One problem with the above-mentioned solutions is that, due to the fact that the strip vibrates, the coating on the strip, after the strip has passed the air-knives, is uneven and that there is thus a need of cost-effective devices and methods for wiping off and stabilizing elongated metallic strips, where the device provides a significant contribution to the layer thickness becoming more uniform across the whole surface of the strip.

SUMMARY OF THE INVENTION

The object of the invention is to provide a device for visual monitoring and stabilization of an elongated metallic strip during continuous transport of the strip in the transport direction along a predetermined transport path where the strip has been coated with a metallic layer by the strip having continuously passed through a bath of molten metal, wherein the strip is intended to be transported from said bath along said predetermined transport path, whereby the device makes a significant contribution to the layer thickness becoming more uniform across the whole surface of the strip.

This object is achieved according to the invention by a device according to the invention described in various claims.

By a predetermined transport path is meant in the following and in the claims an arbitrary plane that may be determined and changed during the transport of the strip, for example when the width or the shape of the strip is being changed. The shape of the strip may, for example, vary with the width of the strip since the strip, when manufacturing the strip by rolling, may experience a deformation and then usually a curved deformation.

An electromagnet comprises a core and at least one coil wound around the core, and in the following and in the claims the length of an electromagnet means the length of the core in the electromagnet.

Further, the object of the invention is achieved by a device comprising at least one electromagnetic stabilizing device comprising at least a pair of electromagnets with at least one electromagnet arranged on respective sides of the strip, designed to stabilize the strip with respect to the predetermined transport path. Further, the device comprises a wiping device for wiping off superfluous molten metal from the strip by applying an air current or gas current in a line across the transport direction of the strip and across essentially the whole width of the strip, wherein the wiping device comprises at least a pair of air-knives arranged with at least one air-knife on each side of the strip.

At least one first image-reading apparatus is arranged in a first region downstream of the wiping device and upstream of the electromagnetic stabilizing device in order to capture, in that region, one or more images of the actual position of the strip in relation to the predetermined transport path.

At least one second image-reading apparatus is arranged in a second region downstream of the wiping device and upstream of the electromagnetic stabilizing device in order to capture, in that region, one or more images of the surface of the strip, and at least one third image-reading apparatus is arranged in a third region downstream of the electromagnetic stabilizing device in order to capture, in that region, one or more images of the surface of the strip.

At least one image-processing unit is adapted, based on the images, captured by the first image-reading apparatus, of the actual position of the strip before the electromagnets, to determine the position of the strip in relation to the predetermined transport path.

The image-processing unit is also adapted, based on the images, captured by the second and third image-reading apparatus, of the surface of the strip taken, respectively, downstream of and upstream of the electromagnetic stabilizing device, to compare the images and then to detect any defects on the strip.

At least one calculating module is adapted, based on the position of the strip determined by the image-processing unit, to calculate the deviation of the strip in relation to the predetermined transport path.

At least one control apparatus is adapted to control a current, in dependence on detected deviations between the strip and the predetermined transport path, to the electromagnets of the electromagnetic stabilizing device in order thus to apply magnetic forces to the strip so that the strip maintains its position in relation to the predetermined transport path.

According to one embodiment of the invention, the third image-reading apparatus is arranged immediately downstream of or in the vicinity of the electromagnetic stabilizing device.

According to one embodiment of the invention, the first image-reading apparatus is arranged downstream of the wiping device and upstream of the electromagnetic stabilizing device in order to capture, during a fixed time interval, one or more images of the position of the strip. In addition, the second image-reading apparatus is arranged downstream of the wiping device and upstream of the electromagnetic stabilizing device in order to capture, during a fixed time interval, one or more images of the surface of the strip. Further, the third image-reading apparatus is arranged downstream of the electromagnetic stabilizing device in order to capture, during a fixed time interval, one or more images of the surface of the strip.

According to one embodiment of the invention, the first image-reading apparatus is arranged downstream of the wiping device and upstream of the electromagnetic stabilizing device in order to continuously film the position of the strip. In addition, the second image-reading apparatus is arranged downstream of the wiping device and upstream of the electromagnetic stabilizing device in order to film the surface of the strip. Further, the third image-reading apparatus is arranged downstream of the electromagnetic stabilizing device in order to film the surface of the strip.

According to one embodiment of the invention, at least one of the first, the second and the third image-reading apparatus comprises at least a still camera, a film camera, a video camera, a web camera, a high-speed camera, or an IR camera.

According to one embodiment of the invention, the device is arranged, for example, in a process line for coating the strip with a layer of metal, whereby said layer is applied by continuous transport of the strip through a bath of molten metal, whereupon air-knives are arranged to blow away any surplus of molten metal from the steel sheet.

According to one embodiment of the invention, the control equipment also controls the current to the coils in the electromagnets of the electromagnetic stabilizing device based on at least one of the following process parameters: the thickness of the strip, the thickness of the layer of molten metal applied to the strip, the width of the strip, the speed of the strip, joints and tensile stress in the strip. Also data from the air-knives, for example the pressure on the gas from the air-knives or the distance between the air-knives and the strip, may be used for guiding the current to the coils in the electromagnets of the electromagnetic stabilizing device.

The object of the invention is achieved also with a method for visual monitoring of an elongated metallic strip during continuous transport of the strip in a transport direction along a predetermined transport path and where the strip is coated with a metallic strip by the strip having continuously passed through a bath of molten metal, according to the features stated in the characterizing part of the independent claim 11.

According to one embodiment of the invention, an elongated metallic strip is transport continuously in a transport direction along a predetermined transport path and the strip is coated with a metallic layer by the strip continuously passing through a bath of molten metal. The strip is transported from the bath of molten metal in a direction along a predetermined transport path and stabilization of the position of the strip with respect to the predetermined transport path occurs in that at least one electromagnetic stabilizing device comprising at least one pair of electromagnets with at least one electromagnets on each side of the strip, where necessary, applies a magnetic force to the strip. Superfluous molten metal is wiped away from the strip by applying an air or gas flow, where the flow is generated by a wiping device comprising an air-knife that is arranged on each side of the strip, to the strip in a line across the transport direction of the strip and across essentially the whole width of the strip. Detection of the position of the strip in relation to the predetermined transport path is carried out by means of a first image-reading apparatus in a first region downstream of the wiping device and upstream of the electromagnetic stabilizing device capturing a plurality of images of the position of the strip, whereupon an image-processing unit is arranged to determine, based on the images captured by the first image-reading apparatus, the actual position of the strip in relation to the predetermined transport path.

Detection of any defects on the surface of the strip is carried out by means of a second image-reading apparatus in a second region, downstream of the wiping device and upstream of the electromagnetic stabilizing device, capturing a plurality of images of the strip, while at the same time a third image-reading apparatus in a third region, downstream of the electromagnetic stabilizing device, captures a plurality of images of the surface of the strip, whereupon an image-processing unit is arranged to detect, based on the images of the surface of the strip captured by the second and third image-reading apparatus, any defects on the surface of the strip.

Then, the calculating module calculates, based on the information from the image-processing unit, the deviation of the strip in relation to the predetermined transport path.

A control apparatus controls the current to the electromagnets of the electromagnetic stabilizing device to thus apply magnetic forces to the strip so that the strip shall maintain its desired position in relation to the predetermined transport path.

According to one embodiment of the invention, in the event of detection of an undesired position on the strip in relation to the predetermined transport path, an operator may manually control the current to the coils in the electromagnets of the electromagnetic stabilizing device so that these move the strip to the desired position and apply a stabilizing force to the strip.

According to one embodiment of the invention, in the event of detection of undesired defects on the surface of the strip detected with the aid of the image-reading apparatus and the image-processing unit, an operator may manually control the flow of air or gas to the air-knives which affects the wiping of molten metal from the strip.

BRIEF DESCRIPTION OF THE DRAWINGS

The invention will be explained in greater detail by description of embodiments with reference to the accompanying drawings, wherein FIG. 1a schematically shows, viewed from the side, an arrangement for applying a coating to a metallic strip, a device for stabilizing the strip, and devices to visually monitor the strip, FIG. 1b shows, as viewed from the front or the back, an embodiment of the invention according to FIG. 1a.

DETAILED DESCRIPTION OF THE INVENTION

The following description relates to the method as well as to the device.

Figure 1A:
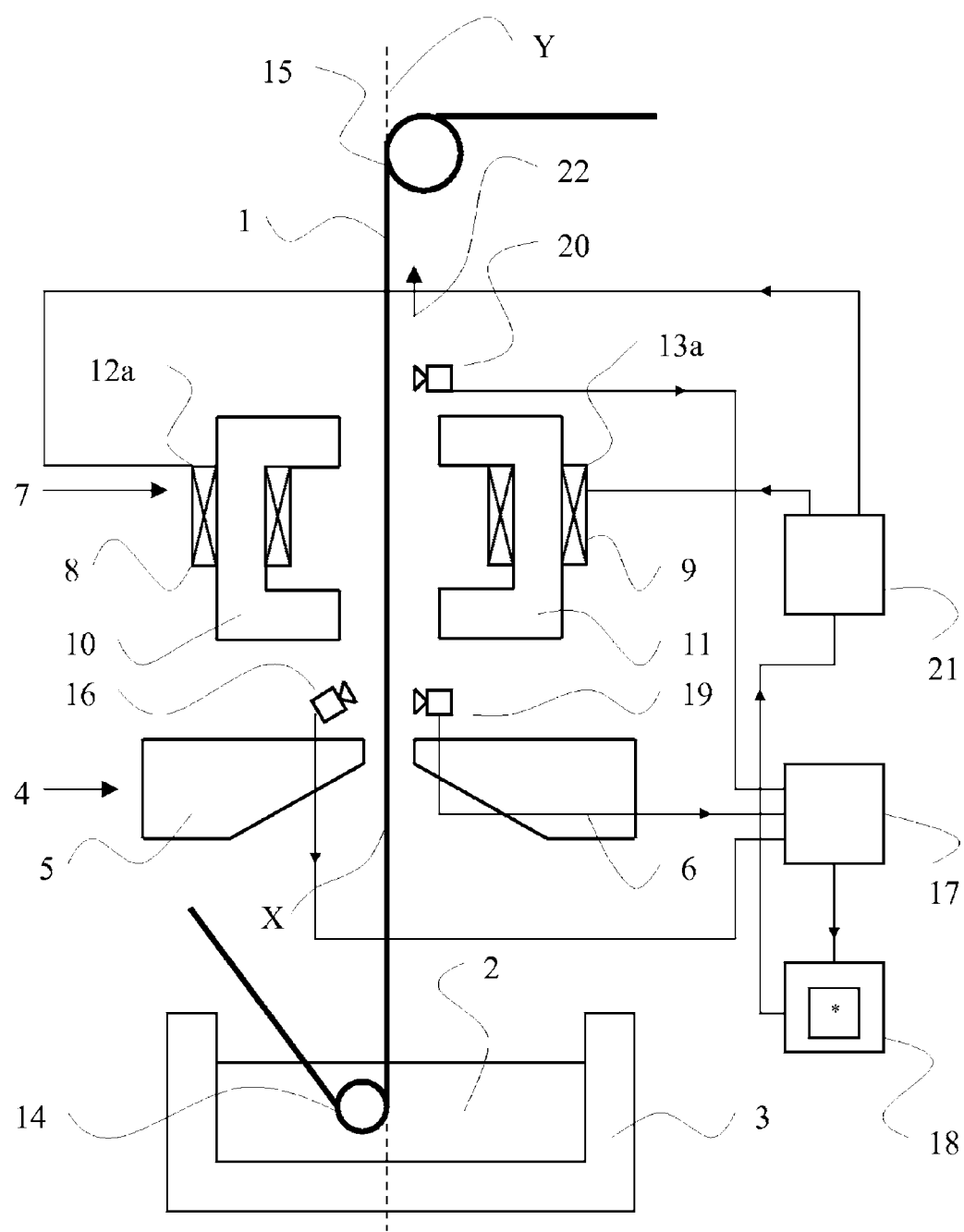

FIG. 1a shows a device for stabilization and visual monitoring of an elongated metallic strip 1 when coating the strip with a layer by the strip being continuously transported through a bath 2 of molten metal in a container 3.

Figure 1B:
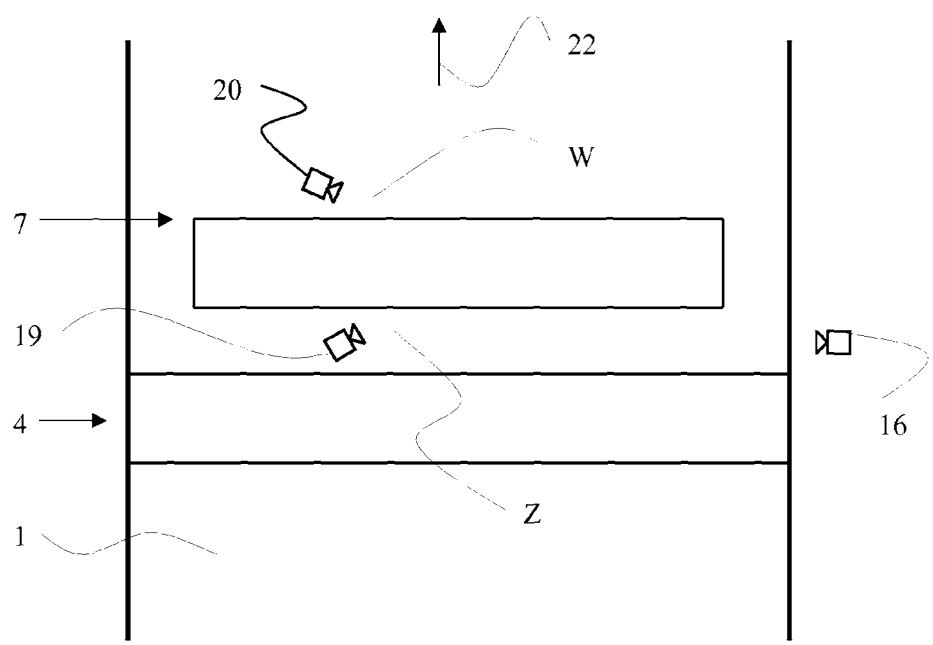

The device comprises a wiping device 4 for wiping off superfluous molten metal from the strip by applying an air current onto the strip and where the wiping device comprises at least one first pair of air-knives 5, 6 with one air-knife arranged on each side of the strip 1. The device also comprises an electromagnetic stabilizing device 7 which is designed to stabilize the position of the strip 1 with respect to a predetermined transport path X. The electromagnetic stabilizing device 7 comprises at least a first pair of electromagnets 8, 9 arranged on one side each of the transport path X. The electromagnets 8, 9 in FIG. 1 each comprise an iron core 10, 11 and two coils 12a-b, 13a-b each; only one coil 12a, 13a in each stabilizing means 8, 9 is visible in FIG. 1. One coil from each electromagnet 8, 9 forms a pair of coils 12a, 13a which are electrically connected to each other and which are controlled together to stabilize the strip. Between a roller 14 immersed in the bath 2 and an upper roller 15 arranged downstream of the stabilizing device 7, the predetermined transport path X mainly extends in a plane Y.

Downstream of the air-knives 5, 6, but upstream of the stabilizing device 7, at least a first image-reading apparatus 16 is arranged in a first region and designed to take images of the position of the strip 1 in relation to the predetermined transport path X in a region that adjoins the line where the air current from the air-knives 5, 6 hits the metal layer on the strip 1. The line-shaped region extends essentially over the whole width of the strip. At least one image-processing unit 17 is configured, based on the images of the position of the strip captured by the first image-reading apparatus 16, to determine and to show on a monitor the actual position of the strip 1 in relation to the predetermined transport path X, whereby an operator 18, by means of a control program in the converter 21, where necessary, controls the currents passing to the stabilizing means, controls the magnetic forces applied by the stabilizing means 8, 9 to the strip in dependence on the actual position, and in a direction perpendicular to the strip.

At least a second image-reading apparatus 19 is arranged in a second region downstream of the air-knives 5, 6 but upstream of the stabilizing device 7 to take images of the surface of the strip in a region Z, and at least a third image-reading apparatus 20 is arranged in a third region downstream of the stabilizing device 7 to take images of the surface of the strip in a region W. The images taken by the second and third image-reading apparatuses, respectively, are processed in the image-processing unit 17, whereby the result is shown on a monitor. The image-processing unit 17 compares the images taken in region Z with the images taken in region W, whereby, if surface defects such as stripes, dots or other contrast variations on the strip are detected by the operator 18, the operator controls the magnetic forces applied to the strip by the stabilizing means 8, 9, thus obtaining an improved surface quality of the strip.

It is also possible for the operator 18 himself, without the help of the image-processing unit 17, to view, on the monitor 18, the images taken by the image-reading apparatuses in regions Z and W, respectively, in order to search for irregular variations such as stripes, dots or other contrast variations on the surface of the strip 1. When necessary, the magnetic forces applied by the stabilizing means 8, 9 on the strip are then controlled, thus obtaining an improved surface quality of the strip.

The invention is not restricted to the embodiments shown, but the skilled person may, of course, modify it in a plurality of ways within the scope of the invention defined by the claims. For example, the strip may be transported in a horizontal direction.

What is claimed is:

1. A device for monitoring and stabilization of an elongated metallic strip during continuous transport of the strip in a transport direction along a predetermined transport path, the device comprising:
    a bath for coating the elongated metallic strip with a metallic layer;
    at least one electromagnetic stabilizing device having at least one first pair of electromagnets with at least one electromagnet arranged on each side of the strip configured to stabilize and/or deform/straighten out the strip with respect to the predetermined transport path;
    a wiping device for wiping off superfluous molten metal from the strip by applying an air current in a line transversely of the transport direction of the strip and across the whole width of the strip, the wiping device having at least one pair of air-knives with at least one air-knife arranged on each side of the strip;
    a first image-reading apparatus arranged in a first region, downstream of and not on the wiping device and upstream of the electromagnetic stabilizing device, and configured to take a plurality of images of the actual position of the strip in relation to the predetermined transport path;
    a second image-reading apparatus arranged in a second region, downstream of and not on the wiping device and upstream of the electromagnetic stabilizing device, and configured to take one or more images of the surface of the strip;
    a third image-reading apparatus is arranged in a third region, downstream of the electromagnetic stabilizing device, and configured to take one or more images of the surface of the strip;
    the third image-reading apparatus arranged downstream of the electromagnets;
    at least one image-processing unit is arranged and configured to determine, based on the images of the position of the strip taken by the first image-reading apparatus, the actual position of the strip in relation to the predetermined transport path, said image-processing unit being also configured to detect, based on the images of the surface of the strip taken with the aid of the second and third image-reading apparatuses, any defects on said surface;
    at least one calculating module configured to calculate, based on the position of the strip determined by the image-processing unit, the deviation of the strip in relation to the predetermined transport path; and
    at least one control apparatus configured to control a current, in dependence on detected deviations between the strip and the predetermined transport path, to the electromagnets of the electromagnetic stabilizing device to apply magnetic forces to the strip so that the elongated metallic strip maintains its position in relation to the predetermined transport path,
    wherein the first image-reading apparatus is configured to take, during a fixed time interval, one or more images of the position of the strip downstream of the wiping device and upstream of the electromagnetic stabilizing device, the second-image reading apparatus also being configured to take, during the fixed time interval, one or more images of the surface of the strip downstream of the wiping device and upstream of the electromagnetic stabilizing device, and the third image-reading apparatus being configured to take, during the fixed time interval, one or more images of the surface of the strip downstream of the electromagnetic stabilizing device.

2. The device of claim 1, wherein at least one of the first, the second and the third image-reading apparatus is in the form of a still camera.

3. The device of claim 1, wherein at least any of the first, the second, and the third image-reading apparatus is in the form of a film or video camera.

4. The device of claim 1, wherein at least one of the first, the second and the third image-reading apparatus is in the form of a web camera.

5. The device of claim 1, wherein at least one of the first, the second and the third image-reading apparatus is in the form of an IR camera.

6. The device of claim 1, wherein at least one of the first, the second and the third image-reading apparatus is in the form of a high-speed camera.

7. The device of claim 1, wherein the image-reading apparatuses consist of a combination of at least two of a still camera, a film camera, a video camera, a web camera, an IR camera, and a high-speed camera.

8. The device of claim 1, wherein the control equipment also controls the current to the electromagnets of the electromagnetic stabilizing device based on at least one of the following process parameters:
    the thickness of the strip,
    the thickness of the layer of molten metal applied onto the strip,
    the width of the strip,
    the speed of the strip, and
    joints and tensile stress in the strip.

* * * * *